United States Patent [19]

Poschel et al.

[11] 4,067,983

[45] Jan. 10, 1978

[54] PHARMACEUTICAL COMPOSITIONS AND METHODS

[75] Inventors: Bruno P. H. Poschel; Donald E. Butler, both of Ann Arbor, Mich.

[73] Assignee: Parke, Davis & Company, Detroit, Mich.

[21] Appl. No.: 751,830

[22] Filed: Dec. 17, 1976

[51] Int. Cl.² ............................................. A61K 31/44
[52] U.S. Cl. .................................. 424/263; 260/297 R
[58] Field of Search ..................... 424/263; 260/297 R

[56] References Cited

U.S. PATENT DOCUMENTS 3,429,689   2/1969   Duerr ................................ 260/297 R

OTHER PUBLICATIONS

Chem. Abst., vol. 75 (1971)–76545a.
Butler et al., J. of Med. Chem. vol. 14, No. 7, pp. 575–579 (1971).

*Primary Examiner*—Stanley J. Friedman
*Attorney, Agent, or Firm*—Stephen Raines; David B. Ehrlinger; Frank S. Chow

[57] ABSTRACT

Oral pharmaceutical compositions comprising 3-phenoxy-pyridine or pharmaceutically acceptable acid-addition salts thereof and a pharmaceutical carrier. Methods for inducing psychostimulation by administering 3-phenoxypyridine or a pharmaceutically acceptable acid-addition salt thereof.

12 Claims, No Drawings

PHARMACEUTICAL COMPOSITIONS AND METHODS

SUMMARY AND DETAILED DESCRIPTION

The present invention relates to oral pharmaceutical compositions possessing psychostimulating properties and to methods for inducing psychostimulation.

More particularly, the invention relates to pharmaceutical compositions and methods employing 3-phenoxypyridine, a known compound which is represented by the formula

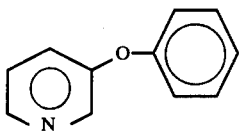

or a pharmaceutically acceptable acid-addition salt thereof. Some typical examples of pharmaceutically acceptable acid-addition salt forms are the hydrochloride, monosulfate, hydrobromide, nitrate, citraconate, maleate, p-toluene sulfonate and methane sulfonate salts. The preferred salt being the monosulfate salt.

In addition, the 3-phenoxypyridine and its acid-addition salts can exist in anhydrous forms as well as in solvated, including hydrated, forms. In general, the hydrated forms and the solvated forms with pharmaceutically-acceptable solvents are equivalent to the anhydrous or unsolvated form for the purposes of the invention. A typical hydrate would be the aforementioned hydrochloride in the form of its hydrate.

In addition, 3-phenoxypyridine compounds may exist in more than one crystalline form, such as the monosulfate, m.p. 114.5°–117° C. and m.p. 107°–109° C., and all forms are intended to be included within the scope of this invention.

In accordance with the invention, oral pharmaceutical compositions are produced by formulating 3-phenoxypyridine or a pharmaceutically acceptable acid-addition salt thereof (as an active ingredient) in dosage unit form with a pharmaceutical carrier. Some examples of dosage unit forms are tablets, capsules, lozenges, and pills; as well as powders and aqueous and non-aqueous solutions and suspensions packaged in containers containing either one or some larger number of dosage units and capable of being sub-divided into individual doses by such means as measurement into a teaspoon or other standard container. Some examples of suitable pharmaceutical carriers, including pharmaceutical diluents, are gelatin capsules; sugars such as lactose and sucrose; starches such as corn starch and potato starch; cellulose derivatives such as sodium carboxymethyl cellulose, ethyl cellulose, methyl cellulose, and cellulose acetate phthalate; gelatin; talc; stearic acid; magnesium stearate; vegetable oils such as peanut oil, cottonseed oil, sesame oil, olive oil, corn oil, and oil of theobroma; propylene glycol; glycerine, sorbitol; polyethylene glycol; water; agar; alginic acid; as well as other compatible substances normally used in pharmaceutical formulations. The compositions of the invention can also contain other components such as coloring agents, flavoring agents, and/or preservatives. These materials, if present, are usually used in relatively small amounts. The compositions can, if desired, also contain other therapeutic agents.

The percentage of the active ingredient in the foregoing compositions can be varied within wide limits but for practical purposes it is preferably present in a concentration of at least 10% in a solid composition and at least 2% in a primarily liquid composition. The most satisfactory compositions are those in which a much higher proportion of the active ingredient is present. The compositions of the invention preferably contain from 1 to 500 mg., preferably 5 to 100 mg. of the active ingredient per dosage unit so that the entire amount to be administered during a day can be made up from a reasonable number of dosage units.

Also in accordance with the invention, 3-phenoxypyridine and pharmaceutically-acceptable acid-addition salts thereof are administered for the purpose of inducing psychostimulation. The term "inducing psychostimulation", as defined in this invention is intended to mean the following:

a. Causing a calming effect in hyperactive individuals, preferably children.

b. Elevation of mood in subjects suffering from mental depression.

c. Increasing the degree of alertness in subjects exhibiting senility or mental fatigue.

By causing a calming effect in hyperactive subjects, preferably children, the subject becomes less prone to distraction and exhibits an enhanced ability to concentrate. Thus the compositions of this invention can be used to improve learning. It should be noted that the compounds may have an independent learning enhancing effect which is unrelated to the calming effect.

The compositions of this invention, by elevating the mood of subjects suffering from mental depression are useful in treating all conditions wherein antidepressants are traditionally employed.

The compositions of this invention, by increasing alertness and attention-focusing ability, are useful in treating senile subjects or normal subjects exhibiting mental fatigue. The aforementioned compounds and compositions are administered orally, in dosage unit form, with the dose adjusted to the needs and tolerances of the individual patient. The usual mammalian dosage range for a 70 kg. subject is from 3.5 to 2,000 mg. per day (0.05 mg. to 29 mg. per kg. of weight per day), preferably 25 to 750 mg. per day (0.36 mg. to 10.7 mg. per kg. of weight per day), optionally in divided portions.

When the aforementioned compounds and compositions of this invention are administered to normal human subjects to overcome fatigue or boredom, dosages on the lower side of the aforementioned dosage range are preferred (3.5 to 500 mg. per day, 0.05 mg. to 7 mg. per kg. per day) while in the treatment of depression dosages on the higher side of the dose range are preferred (1,000 to 2,000 mg. per day, 14 mg. to 29 mg. per kg. of weight per day).

The effectiveness of the aforementioned compounds and compositions is determined by the following tests.

A modified learning and memory test procedure which is generally described in "Psychological Reports", 14 731 (1964) and "Science", 178 518 (1972) is employed.

Eighty male mice are divided into 4 groups of 20 mice each. One hour prior to training, the mice are given 3-phenoxypyridine, dissolved in dilute hydrochloric acid to pH 5.5 to 7.0, intraperitoneally; however, the oral route may also be employed. Usually 3 doses of the chemical are tested at a time, and usually these doses are 5, 20, and 80 mg./kg.

One hour after the above dosing, each mouse is placed, one at a time, on a small shelf attached to the outside wall of a test box. In this position the mouse is suspended in space. Therefore, the mouse is motivated to step from the shelf through a conveniently placed small hole into the interior of the box. As soon as the mouse has all four feet within the semi-darkened interior of the box, the grid floor of the box is electrified (1.5 MA, 3 second duration) to produce a strong pain-fear reaction from the animal. About five seconds thereafter the mouse is removed from the test box and placed in a group holding cage until the entire group has received the single training trial. Then the entire group is returned to the home cages.

One week later, the mice are tested for memory of the painful foot shock received within the shelf-box apparatus. This testing is accomplished by once again placing each mouse on the small shelf attached to the test box. Any mouse that stays on the shelf for 60 seconds without entering the box is counted as remembering the painful foot shock received within the box one week earlier. Any mouse entering the box within the 60-second period is counted as having forgotten the training or as never having learned it in the first place.

The results obtained with placebo and various doses of 3-phenoxypyridine are shown in the following table. When more than one experiment is run at a given dose, the percentage of mice reported as learning and remembering in the table is the mean percentage from all experiments.

| Dose of 3-phenoxy-pyridine mg./kg. | Retention of Learning and Memory (% of mice) |
|---|---|
| Placebo | 70.5 |
| 0.31 | 70 |
| 0.63 | 65 |
| 1.25 | 90 |
| 2.5 | 87.5 |
| 5 | 82.7 |
| 10 | 77.5 |
| 20 | 70 |
| 40 | 50 |
| 80 | 35 |

A second test entitled "Facilitation of Low Base Line Self-Stimulation Screen" is based upon the procedure reported in "Life Sciences", 3 903 (1964).

Adult male albino rats are implanted with permanent electrodes in the medial forebrain bundle of the posterior hypothalamus, an area of the brain which yields intense reward when stimulated. After the animals recover from surgery, they are trained in a Skinner box to press a lever to stimulate their own brains electrically, i.e., to self-stimulate.

After the animals become expert at self-stimulation, the stimulating current is reduced individually for each rat to a level moderately above the reward threshold, which causes self-stimulation rates to decrease correspondingly. Training sessions are run each day under these reduced current conditions until response rates stabilize. The slow response rates generated by these conditions serve as the behavioral base lines. One then proceeds to test whether various treatments increase self-stimulation rates above these base lines. During all tests the self-stimulation behavior of the animals is continuously recorded graphically on cumulative recorders. Drugs, when administered, are given preferably by the oral route.

A drug is considered "active" if the baseline rates of self-stimulation of the animals are clearly augmented by the agent. Such increases in self-stimulation are considered a strong indication that the drug has stimulated the adrenergic reward systems of the brain, and therefore the drug may act favorably upon mental depression.

3-Phenoxypyridine exhibited an excitatory effect on self-stimulation at a dose level of from 5 mg./kg. to 80 mg./kg. (maximum tested dose) with an optimum effect at 20 to 40 mg./kg.

From variations of the above tests it was also observed that there are minimal signs of motor stimulation and no inhibition of monoamine oxidase.

When 3-phenoxypyridine monosulfate is employed in place of 3-phenoxypyridine in the above described self-stimulation screen, similar results are obtained.

The invention is illustrated by the following examples.

EXAMPLE 1

| Ingredient | Quantity |
|---|---|
| 3-Phenoxypyridine Monosulfate | 236 g. |
| Lactose | 1038 g. |
| Corn Starch | 39 g. |
| Hydroxypropyl cellulose | 30 g. |
| Magnesium stearate | 7 g. |
| Ethanol-water 50:50 | q.s. |

The 3-phenoxypyridine monosulfate, lactose and hydroxypropyl cellulose are blended and granulated with 50:50 ethanol-water. The wet granulation is screened, dried and re-screened. The resulting dried granulation is blended with the magnesium stearate and the corn starch, and the mixture is compressed into 225 mg. tablets using 11/32 inch standard concave punches. Yield equals approximately 6,000 tablets, each containing 39.3 mg. of 3-phenoxypyridine monosulfate equivalent to 25 mg. of 3-phenoxypyridine base.

By substituting an equivalent amount of another pharmaceutically acceptable 3-phenoxypyridine salt for the 3-phenoxypyridine monosulfate and adjusting the amount of lactose to give the same total weight in the above formula, there are again obtained 225 mg. tablets each containing the equivalent of 25 mg. of 3-phenoxypyridine base.

EXAMPLE 2

| Ingredient | Quantity |
|---|---|
| 3-Phenoxypyridine Monosulfate | 943 g. |
| Lactose | 1176 g. |
| Corn Starch | 60 g. |
| Hydroxypropyl cellulose | 60 g. |
| Magnesium stearate | 11 g. |
| Ethanol-water 50:50 | q.s. |

The 3-phenoxypyridine monosulfate, lactose and hydroxypropyl cellulose are blended and granulated with 50:50 ethanol-water. The wet granulation is screened, dried and re-screened. The resulting dried granulation is blended with the magnesium stearate and the corn starch, and the mixture is compressed into 375 mg. tablets using 13/32 inch standard concave punches. Yield equals approximately 6,000 tablets, each containing 157.2 mg. of 3-phenoxypyridine monosulfate equivalent to 100 mg. of 3-phenoxypyridine base.

By substituting a equivalent amount of another pharmaceutically acceptable 3-phenoxypyridine salt for the 3-phenoxypyridine monosulfate and adjusting the amount of lactose to give the same total weight in the above formula, there are again obtained 375 mg. tablets, each containing the equivalent of 100 mg. of 3-phenoxypyridine base.

EXAMPLE 3

| Ingredient | Quantity |
| --- | --- |
| 3-Phenoxypyridine Monosulfate | 2358 g. |
| Lactose | 444 g. |
| Corn Starch | 90 g. |
| Hydroxypropyl cellulose | 90 g. |
| Magnesium stearate | 18 g. |
| Ethanol-water 50:50 | q.s. |

The 3-phenoxypyridine monosulfate, lactose and hydroxypropyl cellulose are blended and granulated with 50:50 ethanol-water. The wet granulation is screened, dried and re-screened. The resulting dried granulation is blended with the magnesium stearate and the corn starch, and the mixture is compressed into 500 mg. tablets using ½ inch standard concave punches. Yield equals approximately 6,000 tablets, each containing 393 mg. of 3-phenoxypyridine monosulfate eqivalent to 250 mg. of 3-phenoxypyridine base.

By substituting an equivalent amount of another pharmaceutically acceptable salt of 3-phenoxypyridine for the 3-phenoxypyridine monosulfate and adjusting the amount of lactose to give the same total weight in the above formula, there are again obtained 500 mg. tablets, each containing the equivalent of 250 mg. of 3-phenoxypyridine base.

EXAMPLE 4

| Ingredient | Quantity |
| --- | --- |
| 3-Phenoxypyridine Monosulfate | 393 g. |
| Lactose | 1580 g. |
| Magnesium stearate | 27 g. |

The mixture is blended and filled into No. 4 hard gelatin capsules, filling each capsule with 200 mg. of the powder mixture. Yield equals approximately 10,000 capsules, each containing 39.3 mg. of 3-phenoxypyridine monosulfate equivalent to 25 mg. of 3-phenoxypyridine base.

By substituting an equivalent amount of another pharmaceutically acceptable salt of 3-phenoxypyridine for the 3-phenoxypyridine monosulfate and adjusting the amount of lactose to give the same total weight in the above formula, there are again obtained 200 mg. capsules, each containing the equivalent of 25 mg. of 3-phenoxypyridine base.

EXAMPLE 5

| Ingredient | |
| --- | --- |
| 3-Phenoxypyridine Monosulfate | 1572 g. |
| Lactose | 1540 g. |
| Magnesium stearate | 88 g. |

The mixture is blended and filled into No. 2 hard gelatin capsules, filling each capsule with 320 mg. of the powder mixture. Yield equals approximately 10,000 capsules, each containing 157.2 mg. of 3-phenoxypyridine monosulfate equivalent to 100 mg. of 3-phenoxypyridine base.

By substituting an equivalent amount of another pharmaceutically acceptable salt of 3-phenoxypyridine for the 3-phenoxypyridine monosulfate and adjusting the amount of lactose to give the same total weight in the above formula, there are again obtained 320 mg. capsules, each containing the equivalent of 100 mg. of 3-phenoxypyridine base.

EXAMPLE 6

| Ingredient | Quantity |
| --- | --- |
| 3-Phenoxypyridine Monosulfate | 3930 g. |
| Lactose | 1700 g. |
| Magnesium stearate | 170 g. |

The mixture is blended and filled into No. 0 hard gelatin capsules, filling each capsule with 580 mg. of the powder mixture. Yield equals approximately 10,000 capsules, each containing 393 mg. of 3-phenoxypyridine monosulfate equivalent to 250 mg. of 3-phenoxypyridine base.

By substituting an equivalent amount of another pharmaceutically acceptable 3-phenoxypyridine salt for the 3-phenoxypyridine monosulfate and adjusting the amount of lactose to give the same total weight in the above formula, there are again obtained 580 mg. capsules, each containing the equivalent of 250 mg. of 3-phenoxypyridine base.

EXAMPLE 7

| Ingredient | Quantity |
| --- | --- |
| 3-Phenoxypyridine | 500 g. |
| Polyethylene glycol 400 | 1000 g. |

The above ingredients are blended and filled into soft gelatin capsules, filling each capsule with 300 mg. of the mixture. Yield equals approximately 5,000 capsules, each containing 100 mg. of 3-phenoxypyridine.

Preparation of Acid Addition Salts

A. 3-Phenoxypyridine Hydrochloride

A solution of 10 g. of 3-phenoxypyridine in 10 ml. of 2-propanol is treated with an excess of a solution of dry hydrogen chloride in 2-propanol. The resulting solution is stirred and diluted with ether to give a yellow oil. The oil is separated, triturated several times with ether to give 3-phenoxypyridine hydrochloride as a crystalline solid; m.p. 112°–113.5° C. after recrystallization from 2-propanol-ether followed by drying at reduced pressure.

B. 3-Phenoxypyridine Hydrobromide

A solution of 85 g. of 3-phenoxypyridine in 100 ml. of absolute ethanol is treated with 84 g. of 48% hydrobromic acid with stirring and the solution is evaporated to dryness at reduced pressure. The residue is dissolved in warm 2-propanol, the solution is diluted to cloudiness with ether and chilled to crystallize 3-phenoxypyridine hydrobromide; m.p. 132°–134° C. after drying at reduced pressure.

C. 3-Phenoxypyridine Nitrate

A solution of 9 g. of 3-phenoxypyridine in 20 ml. of absolute ethanol is treated with 9 g. of 70% nitric acid with stirring. The resulting mixture is diluted with 200 ml. of ether and the crystaline precipitate of 3-phenoxypyridine nitrate is collected by filtration, washed with ether and dried at reduced pressure; m.p. 103.5°–105° C.

D. 3-Phenoxypyridine Methanesulfonate

A solution of 18 g. of 3-phenoxypyridine in 100 ml. of 2-propanol is treated with 9.6g. of methanesulfonic acid with stirring. The solution is diluted with ether and the crystalline precipitate of 3-phenoxypyridine methanesulfonate is collected, washed with ether and dried at reduced pressure; m.p. 121°–123° C.

E. 3-Phenoxypyridine p-Toluenesulfonate

A solution of 9 g. of 3-phenoxypyridine in 20 ml. of absolute ethanol is treated with a solution of 9.5 g. of p-toluenesulfonic acid monohydrate in 10 ml. of absolute ethanol with stirring. The resulting solution is evaporated at reduced pressure and the residue triturated with ether to crystallize 3-phenoxypyridine p-toluenesulfonate which is collected by filtration and washed with ether; m.p. 78°–80° C. after recrystallization from 2-propanol.

F. 3-Phenoxypyridine Monosulfate

A solution of 523 g. of 3-phenoxypyridine in 750 ml. of 2-propanol is treated slowly with stirring with 303 g. of 98% sulfuric acid, while maintaining the temperature below 50° C. On cooling to room temperature, the mixture sets up solid. It is heated to 75° C., transferred to an acceptable container and allowed to cool to 50° C. and the crystalline product collected by filtration. The filtrate is allowed to stand at room temperature for 2 hours and the additional crystalline product is collected by filtration. The combined product is dried at reduced pressure to give 3-phenoxypyridine monosulfate, m.p. 103°–107° C. The salt is recrystallized from acetonitrile; after drying at reduced pressure it melts at 107°–109° C.

We claim:

1. A method for inducing psychostimulation in a mammal which comprises administering an effective amount of 3-phenoxypyridine or a pharmaceutically acceptable acid-addition salt thereof to a mammal requiring psychostimulation.

2. The method of claim 1 wherein 0.05 mg. to 29 mg. per kg. per day of said compound is administered.

3. A method for enhancing learning in mammals having learning deficiencies which comprises administering thereto an effective amount of 3-phenoxypyridine or pharmaceutically acceptable acid-addition salts thereof.

4. The method of claim 3 wherein 0.05 mg. to 29 mg. per kg. per day of said compound is administered.

5. A method for calming hyperactive mammals which comprises administering thereto an effective amount of 3-phenoxypyridine or pharmaceutically acceptable acid-addition salts thereof.

6. The method of claim 5 wherein 0.05 mg. to 29 mg. per kg. per day of said compound is administered.

7. A method for treating senility in senile mammals which comprises administering thereto an effective amount of 3-phenoxypyridine or pharmaceutically acceptable acid-addition salts thereof.

8. The method of claim 7 wherein 0.05 mg. to 29 mg. per kg. per day of said compound is administered.

9. A method for treating mental fatigue in mammals suffering from mental fatigue which comprises administering thereto an effective amount of 3-phenoxypyridine or pharmaceutically acceptable acid-addition salts thereof.

10. The method of claim 9 wherein 0.05 mg. to 29 mg. per kg. per day of said compound is administered.

11. A method for treating mental depression in depressed mammals which comprises administering thereto an effective amount of 3-phenoxypyridine or pharmaceutically acceptable acid-addition salts thereof.

12. The method of claim 11 wherein 0.05 mg. to 29 mg. per kg. per day of said compound is administered.

* * * * *